US012673129B2

(12) United States Patent (10) Patent No.: US 12,673,129 B2
Ghodbane et al. (45) Date of Patent: Jul. 7, 2026

(54) SEALANTS FOR TISSUE CLOSURE

(71) Applicant: Ethicon, Inc., Raritan, NJ (US)

(72) Inventors: Salim A. Ghodbane, Piscataway, NJ
(US); Sai Veruva, Raritan, NJ (US);
Mark Neubauer, Raritan, NJ (US)

(73) Assignee: Ethicon, Inc., Raritan, NJ (US)

( * ) Notice: Subject to any disclaimer, the term of this
patent is extended or adjusted under 35
U.S.C. 154(b) by 72 days.

(21) Appl. No.: 17/898,823

(22) Filed: Aug. 30, 2022

(65) Prior Publication Data

US 2024/0066178 A1 Feb. 29, 2024

(51) Int. Cl.
*A61L 24/04* (2006.01)
*A61L 24/00* (2006.01)

(52) U.S. Cl.
CPC ......... *A61L 24/043* (2013.01); *A61L 24/0031*
(2013.01); *A61L 24/0042* (2013.01)

(58) Field of Classification Search
CPC . A61L 24/043; A61L 24/0031; A61L 24/0042
See application file for complete search history.

(56) References Cited

U.S. PATENT DOCUMENTS

| | | | |
|---|---|---|---|
| 5,583,114 | A | 12/1996 | Barrows et al. |
| 6,371,975 | B2 | 4/2002 | Cruise et al. |
| 6,656,496 | B1 | 12/2003 | Kilpadi et al. |
| 8,133,504 | B2 | 3/2012 | Kettlewell et al. |
| 8,846,849 | B2 | 9/2014 | Bordoloi et al. |
| 10,980,913 | B2 | 4/2021 | Dhanaraj et al. |
| 2005/0079999 | A1 | 4/2005 | Wilkie et al. |
| 2015/0005816 | A1 | 1/2015 | Amarpreet et al. |
| 2015/0352246 | A1 | 12/2015 | Henise et al. |
| 2018/0200403 | A1 | 7/2018 | Chang et al. |
| 2019/0269819 | A1* | 9/2019 | Dhanaraj ................ A61L 24/02 |
| 2020/0247101 | A1 | 8/2020 | Shen et al. |

FOREIGN PATENT DOCUMENTS

| | | | |
|---|---|---|---|
| CN | 105778124 A | | 7/2016 |
| WO | 2014116717 A1 | | 7/2014 |
| WO | WO 2014/116717 | * | 7/2017 |
| WO | 2018067938 A1 | | 4/2018 |

OTHER PUBLICATIONS

Serban et al. (J. Biomed Matter Res A. 2011 98(4); 567-575).*
International Search Report for corresponding PCT Application No.
PCT/IB2023/058174, dated Nov. 29, 2023.
Boucard, et al.; "The Use Of Physical Hydrogels Of Chitosan For
Skin Regeneration Following Third-degree Burns"; ScienceDirect;
Biomaterials 28; pp. 3478-3488; 2007.

* cited by examiner

*Primary Examiner* — Shirley V Gembeh
(74) *Attorney, Agent, or Firm* — Meagher Emanuel Laks
Goldberg & Liao, LLP

(57) ABSTRACT

The invention relates to biodegradable bilayer sealants for
tissue closure. The sealants of the invention are composed of
two layers with different compliances. The layer in imme-
diate contact with the tissue has high compliance. The
second layer located immediately above the first sealant
layer has low compliance, i.e. the sealant is much stiffer. The
burst pressure of the bilayer sealants is enhanced relative to
either a single layer elastic sealant or a single layer stiff
sealant. The improved sealant compositions herein provide
a water-tight seal, can access hard to reach tears, be applied
in a dry or wet environment, are low-swelling, and can repair
a range of incision or tear sizes. The bilayer sealants are
particularly useful for sutureless dural closure or as adjuncts
to sutured dural closure. Also provided herein are methods
of preparing and using the biodegradable sealant composi-
tions.

4 Claims, 4 Drawing Sheets

10 dura

CSF $y = -730.99x^2 + 677.21x - 42.845$
$R^2 = 0.9836$

Flexible Hydrogel (% thickness)

Burst Pressure (mm HG)

*FIG. 3*
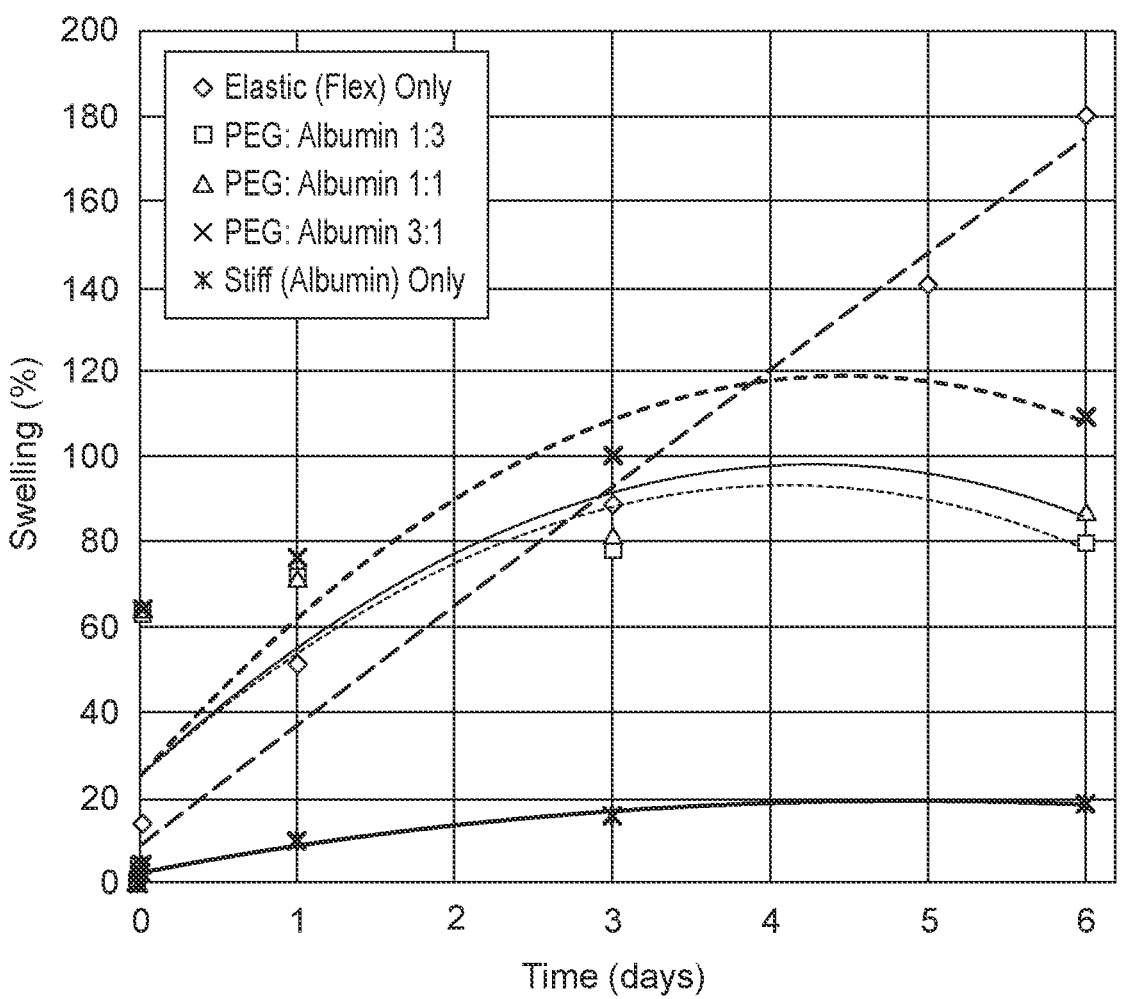

SEALANTS FOR TISSUE CLOSURE

FIELD OF THE INVENTION

The invention relates to biodegradable bilayer sealant compositions for tissue closure, and methods of use thereof.

BACKGROUND

Sutures, patches, implants, and sealants are used for tissue closure of wounds, tears, or surgical incisions. Implantable and biodegradable hydrogel sealants generally exhibit a high degree of swelling which may not be suitable for medical applications around or near sensitive organs and tissues, or in neurosurgery and orthopedic-spine applications. Moreover, there are few desirable sealant options for sealing sutured dural tissue, and currently no sealant options for sutureless dural closure.

Existing polyethylene glycol (PEG) based hydrogel sealants (e.g., DURASEAL, Integra LifeSciences, Princeton, NJ, and ADHERUS, Hyperbranch Medical Technology, Durham, NC) are used as adjuncts to obtain a water tight seal after primary dural tissue closure, e.g., after tissue is sutured. Such existing sealants are intentionally designed to result in high cross-linking densities to reduce swellability, but can have undesirable brittle mechanics. High crosslinking densities are a result of the inclusion of low molecular weight precursors such as trilysine (e.g., in DURASEAL), or substrates such as polyethylenimine (e.g., in ADHERUS), that possess a high density of reactive sites.

There is a need for a tissue closure sealant that creates a water-tight seal, can access hard to reach tears, is low-swelling, flexible, and can repair a range of incision, wound, or tear sizes.

SUMMARY OF THE INVENTION

Surprisingly and unexpectedly, the biodegradable and biocompatible bilayer sealants of the present invention replicate a number of mechanical properties and benefits of an adhesive patch. Provided herein are biodegradable bilayer sealants comprising a first layer having an elastic composition and a second layer having a stiff composition. The elastic layer adheres and conforms to underlying tissue as a result of a compliance similar to tissue, whereas the stiff layer provides reinforcement and constrains swelling of the elastic layer. The bilayer sealants combine the advantages of a standalone elastic or stiff composition. Elastic compositions exhibit a high burst pressure, but a high degree of swelling. Stiff compositions are brittle and provide an inadequate sealant but swell to a lesser degree. As a bilayer, the sealant exhibits both a high burst pressure and low degree of swelling.

The bilayer sealants are useful for difficult to access surgical applications, and medical procedures and surgeries involving sensitive organs and/or tissues, such as, but not limited, to neurosurgery, cranial, spinal, and orthopedic surgeries. Moreover, the bilayer sealants herein are useful for primary and secondary tissue closure, for example, as adjuncts to sutured closures as well as for medical procedures and applications where sutures cannot be used or would not be desirable. The bilayer sealants are particularly useful for sutureless primary dural closure in difficult-to-access suture situations.

In some embodiments, the elastic polymeric composition of the bilayer sealant comprises a hydrogel. In some aspects, the elastic layer comprises a crosslinkable macromolecular polymeric hydrogel. In some embodiments, the elastic polymeric composition comprises a polyethylene glycol (PEG) hydrogel. In some aspects of the invention, the elastic polymeric composition does not include protein.

In other embodiments, the stiff polymeric composition of the bilayer sealant comprises a hydrogel and at least one protein, peptide, or polypeptide. In some aspects, the hydrogel in the stiff layer comprises a PEG hydrogel. In other aspects, the stiff layer comprises one or more reactive macromolecular polymers and at least one protein, peptide, or polypeptide.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds. Polypeptides can also be modified in any of a variety of standard chemical ways (e.g., an amino acid can be modified with a protecting group; the carboxy-terminal amino acid can be made into a terminal amide group; the amino-terminal residue can be modified with groups to, e.g., enhance lipophilicity; or the polypeptide can be chemically glycosylated or otherwise modified to increase stability or in vivo half-life). Polypeptide modifications can include the attachment of another structure such as a cyclic compound or other molecule to the polypeptide and can also include polypeptides that contain one or more amino acids in an altered configuration (i.e., R or S; or, L or D).

The terms "elastic", "flexible", and "flex" are used interchangeably herein.

In other aspects, the stiff polymeric composition comprises a reactive PEG precursor and protein. In some embodiments, the protein in the stiff layer is albumin, fibrinogen, ovalbumin, lactalbumin, extracellular matrix protein, polylysine, collagen, gelatin, or combinations of two or more thereof.

In some aspects, the bilayer sealant is sprayed or dripped on an incision, tear, or wound. In one aspect, two separate single component delivery devices can be used to apply the bilayer sealant to a tissue, or a two component or double barrel delivery device can be used for sequential delivery of the first and second layers of the bilayer sealant. In another aspect, two separate double-barrel delivery devices can be used to prepare each of the elastic polymeric and stiff polymeric compositions, and then apply the elastic polymeric composition and stiff polymeric composition to a tissue.

In another embodiment, methods for tissue closure are provided wherein the elastic polymeric composition is applied to tissue as a liquid solution. After at least partial gelation or curing of the elastic polymeric composition on the tissue, the stiff polymeric composition is applied as a liquid solution onto the elastic polymeric composition, and the bilayers sealant is formed after curing of the elastic and stiff polymeric compositions.

Also provided is a method for tissue closure comprising: (a) applying on a dural tissue a first layer comprising a biodegradable elastic polymeric composition comprising one or more reactive polyethylene glycols; (b) allowing the first layer to at least partially cure; and (c) applying a second layer on a surface of the first layer wherein the second layer comprises a biodegradable stiff polymeric composition comprising one or more reactive polyethylene glycols and a protein. In another aspect, methods for using the biodegradable bilayer sealants of the invention are provided for sutureless dural closure or as adjuncts to sutured dural closure.

In another embodiment of the invention, kits are provided having a first storage container containing a biodegradable elastic polymeric composition component and a second storage container containing a biodegradable stiff polymeric composition component for application to a tissue to form a bilayer sealant wherein the stiff polymeric composition has an elastic modulus of about less than three-fold the elastic polymeric composition.

In another embodiment methods of making the bilayer sealants are provided herein. In one aspect, a method for making a bilayer sealant for tissue closure is provided comprising (a) preparing an elastic polymeric composition comprising combining a first solution comprising a multi-arm PEG and a buffer with a second solution comprising a multi-arm PEG in purified deionized water, and transferring the first and second solutions into separate 5 mL syringes in a first 10 mL double-barrel syringe device; (b) spraying about 1.5 to about 2 mL of the elastic polymeric composition from the first 10 mL double-barrel syringe device on a tissue to create a thickness of about 1.5 mm and allowing the elastic polymeric composition to partially cure; (c) preparing a stiff polymeric composition comprising combining a third solution of albumin in sodium carbonate buffer with a fourth solution of a multi-arm PEG in purified deionized water; (d) transferring each of the third and fourth solutions into separate 5 mL syringes in a second 10 mL double-barrel syringe device (e) spraying about 0.25 mL to about 0.5 mL of the stiff polymeric composition from the second 10 mL double-barrel syringe device on the surface and edges of the partially cured elastic polymeric composition to create a thickness of 0.5 mm and allowing the bilayer sealant to cure.

Provided herein are the aspects and properties of the elastic and stiff polymeric compositions to obtain the novel bilayer sealants.

In some embodiments, numbers expressing quantities of ingredients, properties such as molecular weight, reaction conditions, elastic modulus, elongation at failure, swelling percent, concentrations, and results, and so forth, used to describe and claim certain embodiments of the present disclosure are to be understood as being modified in some instances by the term "about" One of ordinary skill in the art would understand the meaning of the term "about" in the context of the value that it qualifies. In some embodiments, the term "about" is used to indicate that a value includes the standard deviation of the mean for the device or method being employed to determine the value. In some embodiments, the numerical parameters are approximations that can vary depending upon the desired properties sought to be obtained by a particular embodiment. In some embodiments, the numerical parameters should be construed in light of the number of reported significant digits and by applying ordinary rounding techniques.

As used herein, the terms "comprising", "including", "having" and grammatical variants thereof are to be taken as specifying the stated features, integers, steps or components, but do not preclude the addition of one or more additional features, integers, steps, components or groups thereof. These terms encompass the terms "consisting of" and "consisting essentially of". Moreover, as used herein, the indefinite articles "a" and "an" mean "at least one" or "one or more" unless the context clearly dictates otherwise.

These and other aspects and advantages of the present invention will become more apparent from the following description and accompanying figures.

BRIEF DESCRIPTION OF THE DRAWINGS

Figure 1:
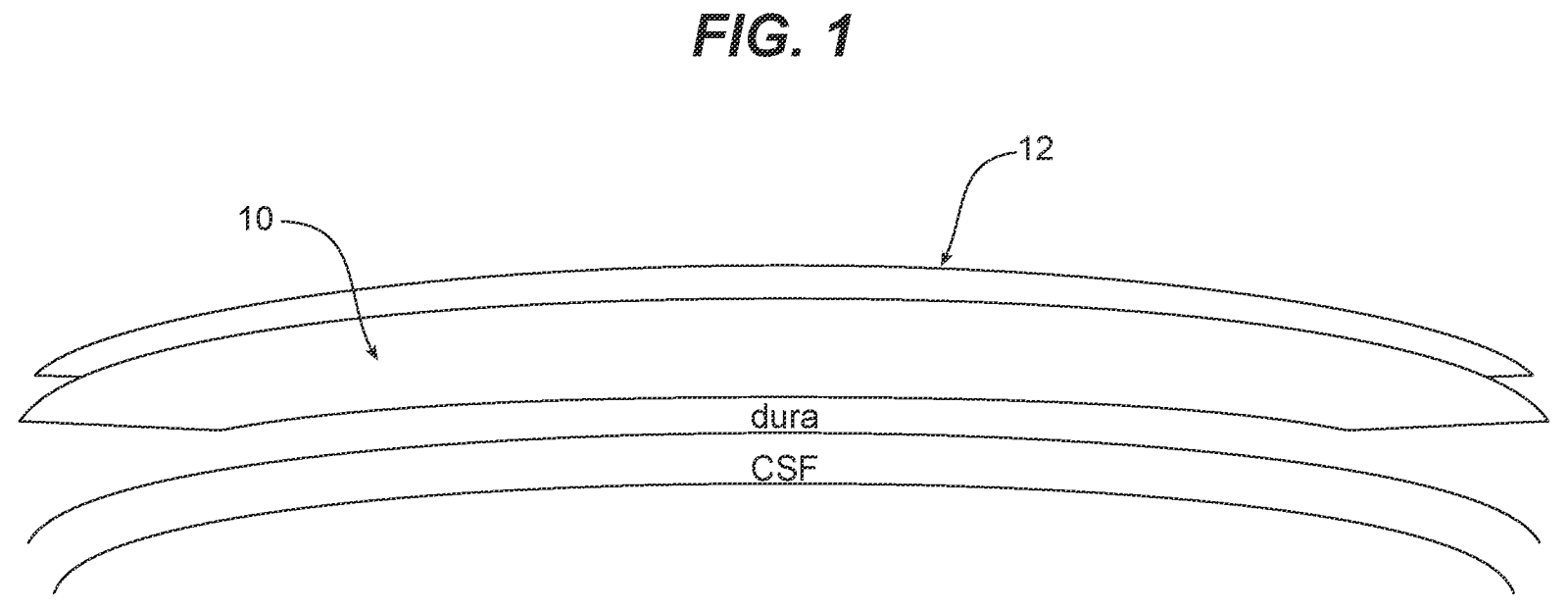

FIG. 1 depicts a cross-section of a bilayer sealant composition of the invention comprising an elastic polymeric composition 10 applied on the dura and a stiff polymeric composition 12 on the elastic polymeric composition.

FIG. 3 is a graph showing the percent of swelling for bilayer sealant compositions of the invention having various ratios of thickness of the elastic layer and stiff layer compositions, and a first control of only an elastic layer composition and a second control of only a stiff layer composition.

DETAILED DESCRIPTION

Figure 2A:
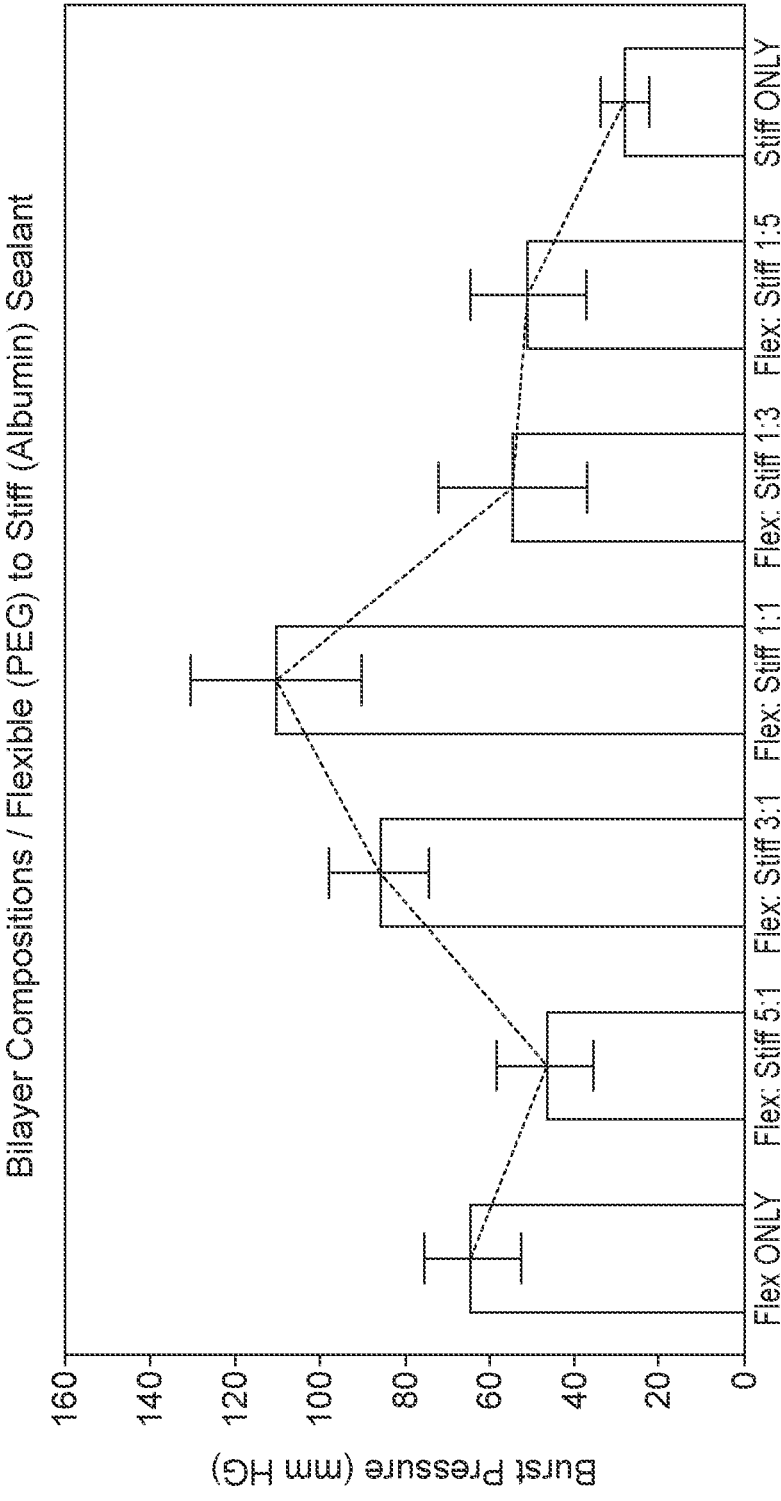
FIG. 2A is a graph showing burst pressure (mmHg) testing of bilayer sealant compositions of the invention at various elastic to stiff layer ratios and a first control composition of only an elastic composition and a second control composition having only a stiff composition.

The present invention is directed to bilayer sealants that replicate a number of the mechanical properties and benefits of an adhesive patch in a liquid sealant. The biodegradable and biocompatible bilayer sealant compositions provided herein can be utilized in difficult-to-access surgical applications. The bilayer sealants adhere to tissue and close tissue tears or incisions without suturing or as adjuncts to sutured tissue. Surprisingly, the bilayer sealants not only provide a durable seal compared to using standalone single layer sealant compositions, but also demonstrate a low extent of swelling. The invention provides bilayer sealants comprising elastic and stiff layers to obtain desirable novel high burst pressure low swelling sealants suitable for sutureless tissue closure.

The dura, dura mater, or dural tissue is connective tissue that protects the brain and spinal cord. It is the outermost layer of the meninges. Dural tissue is subject to tearing and dehydration. Alternatively, dura is sometimes intentionally incised and breached for subdural surgeries. Dural tears and intentional incisions can both result in undesirable leakage of cerebrospinal fluid which can lead to complications such as infections and meningitis.

The bilayer sealants of the invention create a water-tight seal, can be used to repair hard to reach tears, are low swelling, and can repair a range of dural incision or tear sizes. The sealant compositions disclosed herein provide reliability that surgeons desire, particularly, in tissues or areas where suturing is difficult or sutures cannot be used. Moreover, the bilayer sealants may reduce the duration of operating room procedures by eliminating the need to suture dura thereby reducing surgery time. The bilayer sealant compositions simplify dural closure procedures, reduce the length of hospital stays, and minimize post-op complications.

There is a need for a high burst pressure and low swelling sealant for sutured or sutureless tissue closure. Currently available PEG based hydrogel sealants include low molecular weight precursors such as trilysine (e.g., DURASEAL) or substrates, such as polyethylenimine (e.g., ADHERUS), to obtain high cross-linked densities for low swellability, but suffer from the limitation of brittle mechanics. Such brittle mechanics can result in undesirable sealant failure when exposed to pressure peaks, for example, when a patient sneezes, coughs, lifts a heavy object, or is subject to a sudden impact.

The sealants of the invention are composed of two layers with different compliances advantageous for primary dural closure. The elastic polymeric composition in immediate contact with the tissue is flexible and has high compliance similar to dura tissue. The polymeric composition located immediately above the first sealant layer has higher stiffness.

Surprisingly, the biodegradable sealants provided herein have advantageous high burst strength in addition to strong tissue adhesion. The burst pressure of the bilayer sealant is enhanced relative to either a single layer elastic sealant or a single layer stiff sealant. The elastic layer allows the bilayer sealant to mimic the natural mechanics of the dura and conform well to the tissue. On the other hand, the stiff layer provides a level of restriction in strain or elongation to the bilayer sealant. This restriction is advantageous because it prevents the bilayer sealant from straining beyond its extension at failure.

The structural stiffness of a composition is essentially a weighted average by thickness (T) of the elastic modulus (E), i.e., Structural Stiffness $\propto E_{elastic}T_{elastic}+E_{stiff}T_{stiff}$. Therefore, the structural stiffness of the sealant bilayer can be modulated by varying the thickness of each layer. Whereby, when total thickness remains constant, increasing the thickness of the elastic layer will decrease the overall stiffness and increasing the thickness of the stiff layer will increase the overall stiffness. Typically, increased elasticity is correlated with increased swelling. The composite swelling of the bilayer sealants herein can be decreased relative to a single layer elastic sealant composition. The equilibrium of swelling occurs when the osmotic pressure caused by the influx of fluid is balanced by the resulting pressure generated by the strain in polymer molecules. The inclusion of a stiff layer increases resistance to osmotic pressure, resulting in a decreased degree of swelling at equilibrium.

In one embodiment, methods for tissue closure are provided wherein the first elastic polymeric composition is applied to tissue as a liquid solution. After at least partial gelation or curing of the first elastic polymeric composition on the tissue, the stiff polymeric composition is applied as a liquid onto the elastic polymeric composition.

A method for dural tissue closure is provided comprising: (a) applying on a dural tissue a first layer comprising a biodegradable elastic polymeric composition; (b) allowing the first layer to at least partially cure; and (c) applying a second layer on the entire surface of the elastic polymeric composition wherein the second layer comprises a biodegradable stiff polymeric composition.

In one aspect, a method for dural tissue closure is provided comprising: (a) applying on a dural tissue a first layer comprising a biodegradable elastic polymeric composition comprising a polyethylene glycol; (b) allowing the first layer to at least partially cure; and (c) applying a second layer on the entire surface of the elastic polymeric composition wherein the second layer comprises a biodegradable stiff polymeric composition comprising a polyethylene glycol and a protein.

In some embodiments, the bilayer sealant compositions provided herein are formed in situ. In some aspects, the bilayer sealant composition is sprayed or dripped onto the dural defect or incision. In other aspects, the elastic and stiff liquid sealant compositions are applied with a syringe or other applicator. Suitable devices for use in applying the sealants of the invention enable application of the bilayer sealant onto dural tissue, enable uniform application of the bilayer sealant on difficult to access tissue, prevent leakage of the liquid composition by providing a closed volume for containing the fluid, and have a short fluid path thereby eliminating and/or minimizing the risk of inlet blockage due to cross-linking of the fluid. Such devices enable a user, such as a surgeon or other medical practitioner, to uniformly apply the bilayer sealant compositions of the invention without leakage of the substance from the device, and eliminate or reduce the risk of curing or cross-linking of the sealant compositions before they are applied to a tissue. Preferred devices enable a desired volume of sealant to be applied, resulting in a seal of a desired height, width, and length to achieve superior sealing and prevent leakage of cerebrospinal fluid from a dural tear or incision.

Various devices can be used for applying the first and second compositions. For example, two separate single component delivery devices, or a two component or double barrel delivery device can be used for sequential delivery of the first and second layers of the bilayer sealant.

As used herein, the terms "cure" or "curable" in connection with a fluid composition, refers to a composition which can undergo an interaction between its components leading to an increase in viscosity of the composition. Such interactions include polymerization and/or cross-linking of components achieved with or without the use of activating agents such as catalysts, or physical activators such as heat, radiation, e.g., ultraviolet radiation, electron beams, or combinations thereof.

Mixing of the elastic polymeric composition components and contact with proteins/amines at the tissue-interface after application of the elastic polymeric composition on the tissue initiates curing of the elastic sealant and formation of covalent bonds at the tissue interface. Partial gelation time of the elastic layer is approximately 30-60 seconds, after which 0.25-0.5 mL of the stiff polymeric composition is applied by spray or drip covering the entire surface and edges of the elastic layer to create a thickness of 0.5 mm. Mixing of the stiff polymeric composition components and contact with the elastic sealant and tissue-edges will initiate the curing of the stiff sealant; forming covalent bonds at the elastic sealant surface and at the tissue-edge interface.

The elastic layer is expandable, flexible, and has desirable swelling properties. Preferably the elastic polymeric composition is an expandable hydrogel, such as a PEG hydrogel or other macromolecular hydrogel. Biodegradable hydrogels that degrade via hydrolysis are preferred for use in the sealant compositions described herein. In some embodiments, the layers of the bilayer sealant are coupled through functional groups and/or linkers. In some embodiments, the elastic polymeric composition is a hydrogel and the stiff polymeric composition comprises a crosslinker and one or more proteins. In some preferred embodiments, the hydrogel of the elastic polymeric composition is a PEG hydrogel or other macromolecular hydrogel, and the stiff polymeric composition comprises a PEG or other macromolecular hydrogel, and albumin or other suitable protein. In some aspects, the two layers are composed of compatible or mutually reactive chemistries allowing for covalent linkage between the two layers. For example, an ester on a PEG molecule in the elastic polymeric composition forms an amide bond with the protein in the stiff layer.

PEGs suitable for the elastic layer are multi-arm PEGs, such as 2, 3, 4, 6 or 8 multi-arm PEGs. For example, multi-arm PEGs are commercially available from Jenkem Technologies or NOF Corporation. In preferred embodiments, the multi-arm PEG has a molecular weight of about 2 kDa to about 40 kDa. In some embodiments, PEGs suitable for the elastic layer are multi-arm PEGs with reactive functional groups at each termini of the arms, such as N-hydroxysuccinimide (NHS) ester groups. At pH of about 7 to about pH 10, NHS ester groups of the PEG in the elastic layer, and primary amines of the protein in the stiff layer form stable conjugates, i.e, amide bonds. Examples of PEGs for use in the elastic layer are 4-arm-PEG-succinimidyl glutarate (SG), 4-arm-PEG-succinimidyl valerate, 4-arm-PEG-succinimidyl carbonate, 4-arm-PEG-succinimidyl succinate, 4-arm-PEG-succinimidyl butanoate, 4-arm-PEG-succinimidyl succinamide, 4-arm-PEG-succinimidyl propionate, 4-arm-PEG-sulfosuccinimidylglutarate (SG), 4-arm-PEG-sulfosuccinimidylvalerate, 4-arm-PEG-sulfosuccinimidylcarbonate, 4-arm-PEG-succinimidlyl carboxymethyl ester, 4-arm-PEG-sulfosuccinimidylsuccinate, 4-arm-PEG-sulfosuccinimidylbutanoate, 4-arm-PEG-sulfosuccinimidylsuccinamide, 4-arm-PEG-sulfosuccinimidylpropionate, and 4-arm-PEG-isocyanate, 4-arm-PEG-imidoester, and 4-arm-PEG-maleimide. Other examples include linear and 6 arm-PEGs of the chemistries listed above.

In some embodiments, the elastic layer is biosynthetic, for example, the elastic layer can comprise PEG-Amine.

In another aspect, thiols are suitable for use in the stiff layer and are reactive with PEG-NHS esters and PEG-maleimides suitable for use in the elastic layer.

In some embodiments, the elastic layer includes PEGs at a total concentration of from about 80 mg/mL to about 200 mg/mL. In a preferred embodiment the total concentration of PEG is about 124 mg/mL. Examples of preferred PEGs for the elastic layer are 4-arm-PEG-succinimidyl glutarate, M.W. 20,000 (4-arm-PEG-SG-20K) (62 mg/mL) available from JenKem Technologies or NOF Corporation, and 4-arm-PEG-Amine, M.W. 12,000 (4-arm-PEG-NH2 12K) (62 mg/mL) available from Jenkem Technologies or NOF Corporation.

In some embodiments the stiff layer is biosynthetic, or fully biologic such as fibrin, fibrinogen, collagen and/or cellulose formulations.

Albumin for use in the stiff polymeric composition of the bilayer sealants herein are bovine serum albumin (BSA), human serum albumin (HSA), recombinant human albumin, synthetic albumin, and albumin protein variants. Bovine serum albumin (BSA) is commercially available from a number of sources, for example, United States Pharmacopeia (USP) reference standard Bovine Serum Albumin is available from Sigma-Aldrich (St. Louis, Missouri). Recombinant human albumin, USP is commercially available from a number of sources, for example, Sigma-Aldrich (St. Louis, Missouri).

In some embodiments, the stiff layer includes albumin at a concentration of from about 50 mg/mL to about 300 mg/mL. In a preferred embodiment, the concentration of albumin in the stiff layer composition is 150 mg/mL. In another embodiment, the stiff polymeric composition comprises albumin or other suitable protein, and PEG or other macromolecule.

Other proteins suitable for use in the stiff polymeric composition include fibrin, ovalbumin, lactalbumin, collagen, gelatin, extracellular matrix protein, and polylysine.

Other macromolecular cross-linkers for use in hydrogels of the bilayer sealants provided herein include functionalized polyethylene glycol.

In some aspects, the elastic polymeric compositions and stiff polymeric compositions include additional ingredients such as carbonate buffer, phosphate buffer, and phosphate buffered saline. In other aspects, the polymeric compositions herein include a buffer to adjust the pH of the compositions to about pH 7 to about pH 10.

In some embodiments, the total thickness of the bilayer sealant is from about 1.5 mm to about 5.0 mm. The center region of the bilayer sealant application site typically has a slightly thicker application than the edges of the bilayer sealant. The elastic layer is applied by spray or drip to a dural defect with tissue reapproximated at a thickness of 0.9 mm to about 1.95 mm. In some embodiments, thickness of the bilayer sealant applied by spray is from about 1.5 mm to about 2.6 mm. In other embodiments, thickness of the bilayer sealant applied by drip is from about 3.0 mm to about 5.0 mm. For example, for a total bilayer sealant thickness of 2.2 mm applied to dura by spray at a 1:1 ratio would be 1.1 mm elastic layer to 1.1 mm stiff layer. In another aspect, a total bilayer thickness of 2.2 mm applied by spray at a 3:1 ratio would be 1.65 mm elastic layer to 0.55 mm stiff layer.

The gelation time of the elastic layer is approximately 30-60 seconds. The stiff layer can be applied about 1-2 minutes after the elastic layer. The stiff layer is then applied by spray or drip on the surface of the elastic layer at a thickness of about 0.5 mm to about 1.3 mm. Preferred ranges of the mean diameter ratio of the bilayer sealant polymeric compositions provided herein are about 1:1 elastic layer to stiff layer to about 3:1 elastic layer to stiff layer.

In some embodiments, the bilayer sealant degradation occurs in about less than 8 weeks from application.

In another aspect, the biodegradable sealant is characterized by a desirable burst pressure of at least 75 mmHg. For the 3:1 elastic:stiffratio bilayer sealant, the mean burst pressure is about 85.8 mmHg, with a range of about 53.7 mmHg to about 103.9 mmHg. For the 1:1 elastic: stiff ratio bilayer sealant, the mean burst pressure is 110.5 mmHg, with a range of about 32.7 mmHg to about 141.3 mmHg. Existing dural sealants DURASEAL and ADHERUS which are used as adjuncts after primary dural closure have mean burst pressures of about 15.9 mmHg and 25.9 mmHg, respectively.

In another aspect, the elastic modulus (Young's modulus) of the elastic layer in a cured state is about 19.2 kPa to about 24.2 kPa. In one embodiment, the elastic polymeric composition is characterized by an elongation at failure of at least about 300%. In another embodiment, the layer of the stiff polymeric composition is characterized by an elastic modulus less than the elastic layer, such as, about 33.4 kPa to about 47.6 kPa and/or an elongation at failure of about 40% to about 110%.

In a preferred embodiment, the elastic layer is characterized by an ultimate tensile stress of about 40 kPa to about 80 kPa, and an elongation at failure of about 245% to about 508%.

In one aspect, the biodegradable bilayer sealant is characterized by swelling percent of at least about 1.4-fold lower than the swelling percent of a single layer of the elastic polymeric composition having the same thickness, as measured in an aqueous medium such as phosphate buffered saline (PBS) at 37° C. after 6 days. In another aspect, the biodegradable sealant is characterized by swelling percent of about 70% to about 110% as measured in an aqueous medium at 37° C. after 6 days.

In another embodiment, methods of making the bilayer sealants are provided herein. In one aspect, a method of making a bilayer sealant is provided comprising (a) preparing an elastic polymeric composition comprising combining a first solution comprising 124 mg/mL 4-arm-PEG-NH$_2$-20K in about 200 mM N-cyclohexyl-2-aminoethanesulfonic acid (CHES) buffer having a pH of about 9.35 with a second solution comprising 124 mg/mL 4-arm-PEG-succinimidyl glutarate in purified deionized water, and transferring the first and second solutions into separate 5 mL syringes in a first 10 mL double-barrel syringe device; (b) spraying about 1.5 mL to about 2 mL of the elastic polymeric composition from the first 10 mL double-barrel syringe device on a dural tissue to create a thickness of about 1.5 mm and allowing the elastic polymeric composition to partially cure; (c) preparing a stiff polymeric composition comprising combining a third solution of 300 mg/mL bovine serum albumin in about 200 mM sodium carbonate buffer having a pH of about 9.0 with a fourth solution of about 200 mg/mL 4-arm-PEG-succinimidyl glutarate in purified deionized water; (d) transferring each of the third and fourth solutions into separate 5 mL syringes in a second 10 mL double-barrel syringe device (e) spraying about 0.25 mL to about 0.5 mL of the stiff polymeric composition from the second 10 mL double-barrel syringe device onto the surface and edges of the partially cured elastic polymeric composition to create a thickness of 0.5 mm and allowing the bilayer sealant to cure.

In another aspect, the elastic layer is configured to face and adhere to a tissue site. The swelling percent of the bilayer sealants of the invention are particularly advantageous for sealing dural tissue compared to currently available dural sealants such as DURASEAL having a swelling percent of about 200% under comparable conditions.

In one aspect, the bilayer sealants of the present invention provide an antimicrobial impervious barrier. Moreover, the elastic layer of the bilayer sealants provided herein adheres to dural tissue, but advantageously does not adhere to other nearby tissues or organs.

In another embodiment of the invention, kits are provided for application of an elastic polymeric composition and a stiff polymeric composition to a tissue to form a bilayer sealant for tissue closure, wherein the kit comprises a first storage container containing a first solution and a second storage container containing a second solution for preparing a biodegradable elastic polymeric composition component, and a third storage container containing a third solution and fourth storage container containing a fourth solution for preparing a biodegradable stiff polymeric composition component. In some aspects, the elastic polymeric composition component of the kit comprises a polyethylene glycol and the stiff polymeric composition component of the kit comprises a polyethylene glycol and a protein: and wherein the stiff polymeric composition has an elastic modulus of about less than three-fold the elastic polymeric composition after application of the stiff polymeric composition on the surface of the elastic polymeric composition and curing of the compositions. The kit may optionally include four 5 mL syringes and two 10 mL double-barrel syringe devices.

Taken together, the invention covers, inter alia, the following embodiments;

Embodiment 1 of this disclosure relates to a biodegradable bilayer sealant for tissue closure comprising a first layer comprising an elastic polymeric composition and a second layer comprising a stiff polymeric composition wherein the ratio of layer thickness of the elastic polymeric composition to stiff polymer composition is from about 1:1 to about 3:1, respectively.

Embodiment 2: the bilayer sealant according to embodiment 1, wherein the elastic polymeric composition and the stiff polymeric composition are linked by covalent bonds.

Embodiment 3; the bilayer sealant according to embodiment 1 or 2, wherein the elastic polymeric composition and/or the stiff polymeric composition are hydrogels.

Embodiment 4: the bilayer sealant according to embodiment 3, wherein the hydrogels comprise mutually reactive polyethylene glycol.

Embodiment 5: the bilayer sealant according to embodiment 4, wherein the polyethylene glycol is a multi-arm polyethylene glycol.

Embodiment 6: the bilayer sealant according to any one of embodiments 1 to 5, wherein the stiff polymeric composition further comprises a protein or a peptide, and a crosslinker.

Embodiment 7: the bilayer sealant according to embodiment 6, wherein the protein is albumin.

Embodiment 8: the bilayer sealant according to embodiment 7, wherein the albumin is selected from the group consisting of bovine serum albumin, human serum albumin, recombinant human albumin, an albumin protein variant, and synthetic albumin.

Embodiment 9: the bilayer sealant according to embodiment 7, wherein the protein is selected from the group consisting of fibronectin, ovalbumin, lactalbumin, extracellular matrix protein, polylysine, and combinations of two or more thereof.

Embodiment 10: the bilayer sealant according to any one of embodiments 1 to 9, wherein the bilayer sealant has a burst pressure of at least about 80 mmHg.

Embodiment 11: the bilayer sealant according to any one of embodiments 1 to 10, wherein the elastic polymeric composition has an elastic modulus of about 19 kPa to about 24 kPa.

Embodiment 12: the bilayer sealant according to any one of embodiments 1 to 11, wherein the elastic polymeric composition has an elongation at failure of at least about 245%.

Embodiment 13: the bilayer sealant according to any one of embodiments 1 to 12, wherein the stiff polymeric composition has an elastic modulus less than three-fold the elastic polymeric composition and an elongation at failure of about 100/o.

Embodiment 14: the bilayer sealant according to any one of embodiments 1 to 13, wherein the sealant has a swelling percent in an aqueous medium at 37° C. after 6 days at least about 1.4-fold lower than the swelling percent of the elastic polymeric composition having the same thickness in an aqueous medium at 37° C. after 6 days.

Embodiment 15: the bilayer sealant according to any one of embodiments 1 to 14, wherein the sealant has a swelling percent of about 70% to about 110% as measured in an aqueous medium at 37° C. after 6 days.

Embodiment 16 relates to a method for tissue closure, e.g., by making a bilayer sealant, the method comprising: (a) applying on a tissue a first layer comprising a biodegradable elastic polymeric composition comprising a multi-arm polyethylene glycol; (b) allowing the first layer to at least partially cure; and (c) applying a second layer on a surface of the elastic polymeric composition wherein the second layer comprises a biodegradable stiff polymeric composition comprising a multi-arm polyethylene glycol, and a protein or a peptide.

Embodiment 17: the method for tissue closure according to embodiment 16, wherein the multi-arm polyethylene glycol is selected from the group consisting of 4-arm-PEG-amine, 4-arm-PEG-N-hydroxysuccinimide, 6-arm-PEG-N-hydroxysuccinimide, 4-arm-PEG-succinimidyl glutarate, 4-arm-PEG-succinimidyl carbonate, 4-arm-PEG-acrylate, 4-arm-PEG-succinimidyl valerate, 4-arm-PEG-succinimidyl succinate, 4-arm-PEG-succinimidyl butanoate, 4-arm-PEG-succinimidyl succinamide, 4-arm-PEG-succinimidyl propionate, 4-arm-PEG-sulfosuccinimidylglutarate (SG), 4-arm-PEG-sulfosuccinimidylvalerate, 4-arm-PEG-sulfos-uccinimidylcarbonate, 4-arm-PEG-succinimidyl carboxymethyl ester, 4-arm-PEG-sulfosuccinimidylsuccinate, 4-arm-PEG-sulfosuccinimidylbutanoate, 4-arm-PEG-sulfo-succinimidylsuccinamide, 4-arm-PEG-sulfosuccinimidyl-propionate, and 4-arm-PEG-isocyanate, 4-arm-PEG-imidoester, and 4-arm-PEG-maleimide, and combinations of two or more thereof.

Embodiment 18: the method for tissue closure according to embodiment 16 or 17, wherein the protein is selected from the group consisting of albumin, fibronectin, ovalbumin, lactalbumin, extracellular matrix protein, polylysine, and combinations of two or more thereof.

Embodiment 19: the method for tissue closure according to any one of embodiments 16 to 18, wherein the ratio of layer thickness of the elastic polymeric composition to stiff polymer composition is from about 1:1 to about 3:1; the elastic polymeric composition has an elastic modulus of about 19 kPa to about 24 kPa; and the stiff polymeric composition has an elastic modulus about less than three-fold the elastic polymeric composition.

Embodiment 20 relates to a kit for preparing a biodegradable bilayer sealant for closure of a tissue comprising a first storage container containing a first solution comprising a multi-arm PEG in cyclohexyl-2-aminoethanesulfonic acid (CHES) buffer and a second storage container containing a second solution comprising a multi-arm PEG in purified deionized water for preparing a biodegradable elastic polymeric composition component; a third storage container containing a third solution comprising a protein or peptide in sodium carbonate buffer and a fourth storage container containing a fourth solution comprising multi-arm PEG in purified deionized water for preparing a biodegradable stiff polymeric composition component; and wherein after application of the stiff polymeric composition on the surface of the elastic polymeric composition, and curing of the elastic polymeric composition and stiff polymeric composition, the stiff polymeric composition has an elastic modulus of about less than three-fold the elastic polymeric composition.

Embodiment 21 relates to a method of making a bilayer sealant for tissue closure comprising (a) preparing an elastic polymeric composition comprising combining a first solution comprising about 80 mg/mL to about 200 mg/mL PEG-NH$_2$-20K in about 200 mM N-cyclohexyl-2-aminoeth-anesulfonic acid (CHES) buffer having a pH of about 9.35 with a second solution comprising about 80 mg/mL to about 200 mg/mL 4-arm-PEG-succinimidyl glutarate in purified deionized water, and transferring the first and second solutions into separate 5 mL syringes in a first 10 mL double-barrel syringe device; (b) spraying about 1.5 mL to about 2 mL of the elastic polymeric composition from the first 10 mL double-barrel syringe device on a tissue to create a thickness of about 1.5 mm and allowing the elastic polymeric composition to partially cure; (c) preparing a stiff polymeric composition comprising combining a third solution of about 50 mg/mL to about 300 mg/mL bovine serum albumin in about 200 mM sodium carbonate buffer having a pH of about 9.0 with a fourth solution of 80 mg/mL to about 200 mg/mL 4-arm-PEG-succinimidyl glutarate in purified deionized water; (d) transferring each of the third and fourth solutions into separate 5 mL syringes in a second 10 mL double-barrel syringe device; and (e) spraying about 0.25 mL to about 0.5 mL of the stiff polymeric composition from the second 10 mL double-barrel syringe onto the surface and edges of the partially cured elastic polymeric composition to create a thickness of about 0.5 mm and allowing the bilayer sealant to cure.

Additional details with regard to the inventive bilayer sealants are provided in the following non-limiting examples.

EXAMPLES

The following materials were procured for preparing and testing the bilayer sealant. 4-arm PEG-Amine, M.W. 20,000 (4-arm-PEG-NH2-20K) from JenKem Technologies; 4-arm-PEG-succinimidyl glutarate, M.W. 20,000 (4-arm-PEG-SG-20K) from JenKem Technologies; bovine serum albumin from Sigma, sodium carbonate from Sigma; and, N-Cyclo-hexyl-2-aminoethanesulfonic acid (CHES) from Sigma. Testing equipment included a pressure gauge (IP-073), timer (EC-203), caliper (ID-0164) and standard syringe pump.

Example 1

Preparation of Elastic Polymeric Composition of Bilayer Sealant

To prepare the elastic polymeric composition of the bilayer sealant, first, 124 mg/mL 4-arm-PEG-Amine, M.W. 20,000 (4-arm-PEG-NH2-20K), solution is prepared in 200 mM N-Cyclohexyl-2-aminoethanesulfonic acid (CHES) buffer having a pH of about 9.35. Next, 124 mg/mL 4-arm-PEG-succinimidyl glutarate, M.W. 20,000 (4-arm-PEG-SG-20K), solution is prepared in purified deionized (DI) water. Each solution is then transferred into separate 5 mL Luer-Lok syringes to set up a 10 mL double-barrel syringe device with a mixing tip, ready for timely expression. The final concentration of the mixed elastic polymeric composition is 62 mg/mL 4-arm-PEG-NHS-20K, 100 mM CHES, and 62 mg/mL 4-arm-PEG-SG-20K.

Example 2

Preparation of Stiff Polymeric Composition of Bilayer Sealant

To prepare the stiff polymeric composition of bilayer sealant, first, 300 mg/mL bovine serum albumin, M.W. ~66 kDa (BSA), solution is prepared in 200 mM sodium carbonate buffer having a pH of about 9.0. Next, 200 mg/mL 4-arm-PEG-succinimidyl glutarate, M.W. 10,000 (4-arm-PEG-SG-10K), solution is prepared in purified DI water. Each solution is then transferred into separate 5 mL Luer-Lok syringes to set up a 10 mL double-barrel syringe device with a mixing tip, ready for timely expression. The final concentration in mixed sealant is 150 mg/mL BSA, 100 mM sodium carbonate, and 100 mg/mL 4-arm-PEG-SG-10K.

Example 3

Application of First Elastic and Second Stiff Polymeric Compositions to Form Bilayer Sealant After both the elastic and stiff polymeric compositions are prepared in 10 mL double-barrel syringe devices, the former is expressed from the double-barrel syringe first. Over a 15 mm linear dural/tissue tear that is reapproximated, about 1.5 mL to about 2 mL of the elastic sealant is applied via spray or drip mixing tips to create a thickness of about 1.5 mm. The mixing of components and contact with proteins/amines at the tissue-interface will initiate the curing of the elastic sealant; forming covalent bonds at the tissue interface. The partial gelation time of this elastic layer is approximately 30-60 seconds, after which the stiff sealant can be applied next. 0.25 mL-0.5 mL of the stiff layer is then applied by spray or drip covering the entire surface and edges of the elastic layer to create a thickness of 0.5 mm. The mixing of the stiff sealant components and contact with proteins/ amines on the elastic sealant and tissue-edges will initiate the curing of the stiff sealant: forming covalent bonds at the elastic sealant surface and at the tissue-edge interface. The mean diameter ratio of the bilayer sealant polymeric compositions after curing is about 3.1 elastic layer to stiff layer. After 30-60 seconds are elapsed, the elastic and stiff polymeric compositions are interconnected, and the bilayer sealant is formed and continues to cure/strengthen over the next 10 minutes.

Example 4

Burst Pressure Test of Sealant Compositions

Various sealant compositions were tested in a benchtop dura burst pressure assessment to evaluate various ratios of elastic polymeric composition to stiff polymeric composition. A linear incision of 15 mm in length was created in harvested porcine dura and reapproximated to simulate a clinical dural tear condition. Next, 1.5 mL-2.0 mL or 1.5 mm-2 mm thickness of an elastic polymeric composition and a stiff polymeric composition were separately tested as controls. The thickness of each layer was modulated by varying the volume of each polymeric composition applied to a constant tissue area. A syringe pump was used to create the pressure below the tissue surface at an infusion rate of 2-10 ml/min and was tested until failure. The peak pressure at failure and failure mode was recorded for each sample. The failure modes were defined as cohesive, failure within the sealant, or adhesive, failure at the sealant and tissue interface. The results for the burst pressure test are shown in Table 1 below and the graph in FIG. 2A showing burst pressure (mmHg) testing results of bilayer sealants of the invention at various elastic to stiff layer ratios and a first control composition of only the elastic polymeric composition and a second control composition having only the stiff polymeric composition. Preferred ranges of the mean diameter ratio of the bilayer sealant polymeric compositions provided are about 1:1 elastic layer to stiff layer to about 3:1 elastic layer to stiff layer in comparison to the controls.

TABLE 1

| Ratio of Elastic (Flex) to Stiff Polymeric Composition | Elastic Layer (% thickness) | Burst Pressure (mmHg) | Standard Deviation (mmHg) |
| --- | --- | --- | --- |
| Elastic Only | 100 | 64.1 mmHg | 22.0 |
| Elastic:Stiff 5:1 | 83 | 46.5 mmHg | 23.1 |
| Elastic:Stiff 3:1 | 75 | 85.8 mmHg | 23.5 |
| Elastic:Stiff 1:1 | 50 | 110.5 mmHg | 45.7 |
| Elastic:Stiff 1:3 | 25 | 54.6 mmHg | 40.1 |
| Elastic:Stiff 1:5 | 17 | 51.0 mmHg | 26.9 |
| Stiff Only | 0 | 28.2 mmHg | 10.2 |

Figure 2B:
FIG. 2B is a graph of normal distribution showing burst pressure at various percent thickness of the elastic (flexible hydrogel) layer of the bilayer compositions of the invention.

The results of the burst pressure test of bilayer sealants at various percent thickness of the elastic layer with respect to the total bilayer sealant thickness are shown in the graph in FIG. 2B.

It was observed that an elastic polymeric composition thickness of about 50% resulted in an increased burst pressure relative to controls or bilayer sealants with less than or greater than 50% elastic polymeric composition.

Example 5

Swelling Test of Sealant Compositions

The extent of swelling of sealant compositions having various ratios of elastic polymeric composition to stiff polymeric composition. The sealant compositions were applied to a cylindrical mold and allowed to fully cure. The sealant compositions were then soaked in PBS at 37° C. for 6 days. Swelling percent of the sealant compositions was assessed on days 1 through 6 based on gravimetric measurements. The elastic polymeric composition alone swelled to 180%. The stiff polymeric composition alone swelled to 20%. Surprisingly, with as little as 33% of the thickness of the bilayer composed of the stiff polymeric composition, the extent of swelling was reduced to about 100% (about 57% of the swelling observed in the elastic formulation alone). The results for the swelling test are shown in Table 2 below and the graph in FIG. 3.

TABLE 2

| Ratio of Elastic (Flex) to Stiff Polymeric Composition | Time (Days) | Swelling (%) |
| --- | --- | --- |
| Elastic (Flex) Only | 1 | 51.13 |
| Elastic (Flex) Only | 3 | 88.10 |
| Elastic (Flex) Only | 6 | 180.26 |
| PEG:Albumin 1:3 | 1 | 71.64 |
| PEG:Albumin 1:3 | 3 | 78.29 |
| PEG:Albumin 1:3 | 6 | 80.25 |
| PEG:Albumin 1:1 | 1 | 72.22 |
| PEG:Albumin 1:1 | 3 | 81.70 |
| PEG:Albumin 1:1 | 6 | 87.69 |
| PEG Albumin 3:1 | 1 | 76.65 |
| PEG Albumin 3:1 | 3 | 100.39 |
| PEG Albumin 3:1 | 6 | 109.91 |
| Stiff Albumin Only | 1 | 10.03 |
| Stiff Albumin Only | 3 | 16.09 |
| Stiff Albumin Only | 6 | 18.56 |

Example 6

Evaluation of Elastic and Stiff Sealant Formulation Tensile Properties

To prepare the elastic polymeric composition of the bilayer sealant, first, 124 mg/mL 4-arm-PEG-Amine, M.W. 20,000, solution is prepared in 200 mM N-Cyclohexyl 2aminoethanesulfonic acid (CHES) buffer at 9.35 pH. Next, 124 mg/mL 4-arm-PEG-succinimidyl glutarate, M.W. 20,000, solution is prepared in purified deionized (DI) water. The final concentration of the mixed elastic polymeric composition is 62 mg/mL 4-arm-PEG-NHS-20K, 100 mM CHES, and 62 mg/mL 4-arm-PEG SG-20K.

A Sulzer mixing drip tip was attached to the device, the device was primed, and then immediately expressed into 5 tensile molds. The samples were loaded onto an Instron test machine and tested after a 10-minute cure time. The test was completed with a 10 N load cell, molds to ensure a gauge length of 14.8 mm and cross-sectional area of 18.29 mm$^2$, and tested with a rate of 40.0 mm/min. The results of this study are shown in Table 3 below.

TABLE 3

| Formulation | Average Maximum Load (kPa) | | Average Percent Elongation (%) | | Modulus of Elasticity (kPa) | |
|---|---|---|---|---|---|---|
| | Mean | SD | Mean | SD | Mean | SD |
| Elastic | 77.3 | 15.8 | 316 | 50 | 21.7 | 2.5 |
| Stiff | 28.1 | 3.6 | 58 | 12 | 40.5 | 7.1 |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for tissue closure comprising:
   (a) spraying on a tissue a first layer comprising a biodegradable elastic polymeric composition comprising a multi-arm polyethylene glycol;
   (b) allowing the first layer to at least partially cure; and
   (c) spraying a second layer on a surface of the biodegradable elastic polymeric composition wherein the second layer comprises a biodegradable stiff polymeric composition comprising a multi-arm polyethylene glycol, and a protein or a peptide,
   wherein a ratio of layer thickness of the biodegradable elastic polymeric composition to stiff polymer composition is from about 1:1 to about 3:1; the biodegradable elastic polymeric composition has an elastic modulus of about 19 kPa to about 24 kPa; and the biodegradable stiff polymeric composition has an elastic modulus about less than three-fold the biodegradable elastic polymeric composition;
   wherein the first layer and second layer are composed of compatible chemistries, allowing for covalent linkage between the first layer and second layer,
   wherein the elastic polymeric composition is characterized by an elongation at failure of at least about 245%, and wherein the stiff polymeric composition is characterized by an elongation at failure of up to about 110%.

2. The method of claim 1, wherein the multi-arm polyethylene glycol is selected from the group consisting of 4-arm-PEG-amine, 4-arm-PEG-N-hydroxysuccinimide, 6-arm-PEG-N-hydroxysuccinimide, 4-arm-PEG-succinimidyl glutarate, 4-arm-PEG-succinimidyl carbonate, 4-arm-PEG-acrylate, 4-arm-PEG-succinimidyl valerate, 4-arm-PEG-succinimidyl succinate, 4-arm-PEG-succinimidyl butanoate, 4-arm-PEG-succinimidyl succinamide, 4-arm-PEG-succinimidyl propionate, 4-arm-PEG-sulfosuccinimidylglutarate (SG), 4-arm-PEG-sulfosuccinimidylvalerate, 4-arm-PEG-sulfosuccinimidylcarbonate, 4-arm-PEG-succinimidyl carboxymethyl ester, 4-arm-PEG-sulfosuccinimidylsuccinate, 4-arm-PEG-sulfosuccinimidylbutanoate, 4-arm-PEG-sulfosuccinimidylsuccinamide, 4-arm-PEG-sulfosuccinimidylpropionate, and 4-arm-PEG-isocyanate, 4-arm-PEG-imidoester, and 4-arm-PEG-maleimide, and combinations of two or more thereof.

3. The method of claim 1, wherein the protein is selected from the group consisting of albumin, fibronectin, ovalbumin, lactalbumin, extracellular matrix protein, polylysine, and combinations of two or more thereof.

4. The method of claim 1, wherein the biodegradable elastic polymeric composition consists of a 4-arm PEG-Amine, a 4-arm-PEG-succinimidyl glutarate (PEG-SG), water, and a buffer, and wherein the biodegradable stiff polymeric composition consists of albumin, PEG-SG, water, and a buffer.

* * * * *